United States Patent [19]
Takai et al.

[11] Patent Number: 5,705,249
[45] Date of Patent: Jan. 6, 1998

[54] LIQUID-PERMEABLE COMPOSITE NONWOVEN FABRIC FOR USE IN BODY FLUIDS ABSORPTIVE ARTICLES

[75] Inventors: Hisashi Takai; Hideki Kondo, both of Ehime-ken; Tomoko Tsuji, Kagawa-ken, all of Japan

[73] Assignee: Uni-Charm Corporation, Ehime-ken, Japan

[21] Appl. No.: 590,979

[22] Filed: Jan. 24, 1996

[30] Foreign Application Priority Data

Jan. 26, 1995 [JP] Japan .................................. 7-010946

[51] Int. Cl.⁶ ...................................................... B32B 5/08
[52] U.S. Cl. ........................... 428/94; 428/175; 428/179; 428/182; 428/184; 428/189; 428/297.7; 428/298.1; 428/299.7; 442/366; 604/384; 604/385.1
[58] Field of Search .............................. 428/232, 175, 428/179, 182, 183, 184, 85, 92, 93, 94, 189, 297.7, 298.1, 299.7; 442/366

[56] References Cited

U.S. PATENT DOCUMENTS

| 3,665,922 | 5/1972 | Skora . |
| 3,967,623 | 7/1976 | Butterworth et al. . |

FOREIGN PATENT DOCUMENTS

| 57-82505 | 5/1982 | Japan . |
| 9515138 | 8/1995 | WIPO . |

Primary Examiner—Marion E. McCamish
Assistant Examiner—Elizabeth M. Cole
Attorney, Agent, or Firm—Lowe, Price, LeBlanc & Becker

[57] ABSTRACT

The liquid-permeable composite nonwoven fabric for use in the body fluids absorptive articles such as sanitary napkins comprises a liquid-permeable nonwoven fabric made from thermoplastic synthetic fibres and a plurality of continuous filaments made from thermoplastic synthetic resin being arranged parallel to one another and bonded to an upper surface of the nonwoven fabric at bonding zones arranged intermittently along and longitudinally of the respective filaments so that each filament may form bulges describing circular arcs above the nonwoven fabric.

6 Claims, 4 Drawing Sheets

LIQUID-PERMEABLE COMPOSITE NONWOVEN FABRIC FOR USE IN BODY FLUIDS ABSORPTIVE ARTICLES

BACKGROUND OF THE INVENTION

The present invention relates liquid-permeable composite nonwoven fabric for use in body fluids absorptive articles such as disposable diapers, training pants and sanitary napkins or menstruation pads.

It is well known in the body fluids absorptive articles such as disposable diapers to employ a composite nonwoven fabric comprising a nonwoven fabric and a plurality of continuous filaments bonded to an upper surface of the nonwoven fabric as a liquid-permeable topsheet thereof. For example, Japanese Laid-Open Patent Application No. Sho57-82505 discloses a technique of placing a hydrophobic netty sheet composed of a plurality of continuous filaments on a hydrophilic sheet and embossing these two sheets together to form a composite nonwoven fabric having its upper layer defined by the netty sheet, which is employed as the topsheet. In accordance with this known technique, the netty sheet is obtained by forming a so-called inflation film which has been extruded through the round dies. Specific materials for the above-mentioned hydrophilic sheet may be selected from those containing, as its main ingredient, hydrophilic cellulosic materials such as pulp, rayon and cotton.

While the composite nonwoven fabric obtained by the prior art has a hydrophobic nature, absorptivity and strength required for the topsheet of body fluids absorptive articles, the users often dislike such known composite nonwoven fabric, since each of the continuous filaments is really torn up from a film and has a flat surface which gives the users a somewhat sticky feeling peculiar to plastics when these filaments come in contact with the skin. Furthermore, the prior art teaches a manner of embossing the netty sheet together with the hydrophilic sheet by which these two sheets bite into each other or one of which bites into the other. With the nonwoven fabric obtained in this manner, the surface of the netty sheet loses its initial rough touch and becomes smooth. In consequence, not only the undesirable sticky feeling is further enhanced but also an adequate cushioning effect and softness both being desired for the topsheet can not be expected.

SUMMARY OF THE INVENTION

Accordingly, it is a principal object of the invention to solve the problem as described above by bonding a plurality of filaments extending parallel to one another to an upper surface of a nonwoven fabric at bonding zones intermittently arranged longitudinally of each filament so that the filament may form between each pair of adjacent bonding zones along this filament a bulge describing a circular arc above the upper surface of the nonwoven fabric.

The object set forth above is achieved, according to the invention, by a liquid-permeable composite nonwoven fabric for use in body fluids absorptive articles comprising a liquid-permeable nonwoven fabric including thermoplastic synthetic fibres and a plurality of continuous filaments made of thermoplastic synthetic resin and bonded to an upper surface of the liquid-permeable nonwoven fabric, wherein the filaments extend parallel to one another and each of the filaments is fixed to the upper surface of the nonwoven fabric at bonding zones intermittently arranged longitudinally thereof so as to form between each pair of adjacent the bonding zones a bulge describing a circular-arc above the upper surface of the nonwoven fabric and having a substantially circular shape in its radial cross-section.

Preferably, the filaments are welded to the upper surface of the nonwoven fabric at the bonding zones. The composite nonwoven fabric of the invention may be composed of the filaments and nonwoven fabric both being hydrophobic. Alternatively, the composite nonwoven fabric may be composed of the filaments being hydrophobic and the nonwoven fabric being hydrophilic.

With the liquid-permeable composite nonwoven fabric for use in body fluids absorptive articles constructed in the manner as described above, the bulges of the respective filaments describing the circular arcs above the upper surface of the nonwoven fabric provides a cushioning effect and softness both desired for such articles by repeating elastic deformation and restoration as the bulges come in and off from contact with the wearer's skin. The composite nonwoven fabric comes in contact with the wearer's skin practically at tops of the respective filament bulges each being substantially circular in its radial cross-section. In other words, a total area of the composite nonwoven fabric coming in contact with the wearer's skin when the body fluids absorptive article is put on the wearer's body is relatively small and, therefore, an undesirable sticky feeling peculiar to a plastic product such as a plastic film can be effectively alleviated.

DESCRIPTION OF THE PREFERRED EMBODIMENT

Figure 1:
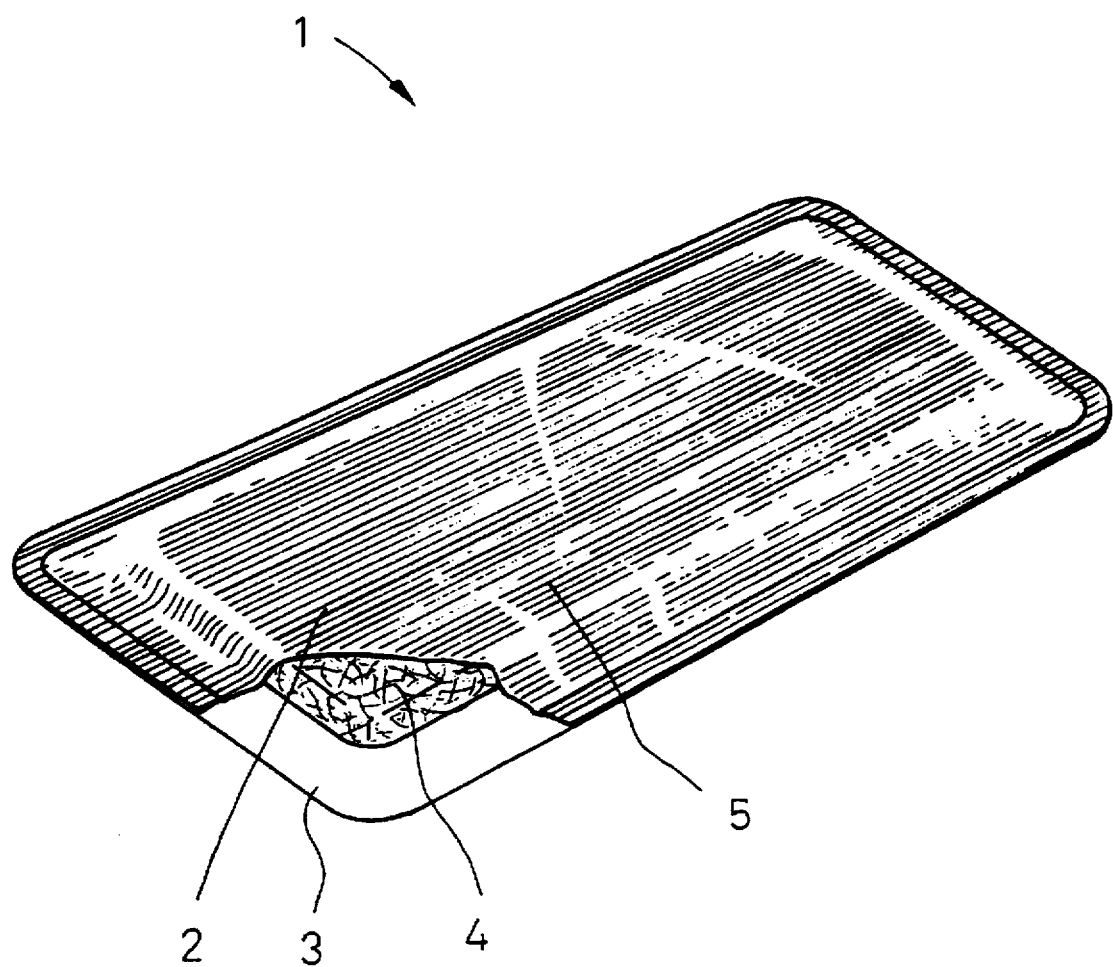
FIG. 1 is a perspective view showing a body fluids absorptive article on which a composite nonwoven fabric of the present invention is employed, as partially broken away.

Referring to FIG. 1, a sanitary napkin 1 as an example of body fluids absorptive articles comprises a liquid-permeable topsheet 2, a liquid-impermeable backsheet 3 and a liquid-absorbent core 4 disposed between these two sheets 2, 3. The top- and backsheets 2, 3 are jointed to each other along their portions extending outward beyond a peripheral edge of the core 4. The topsheet 2 carries on its upper surface a plurality of continuous filaments 5 extending parallel to one another longitudinally of the topsheet 2.

Figure 2:
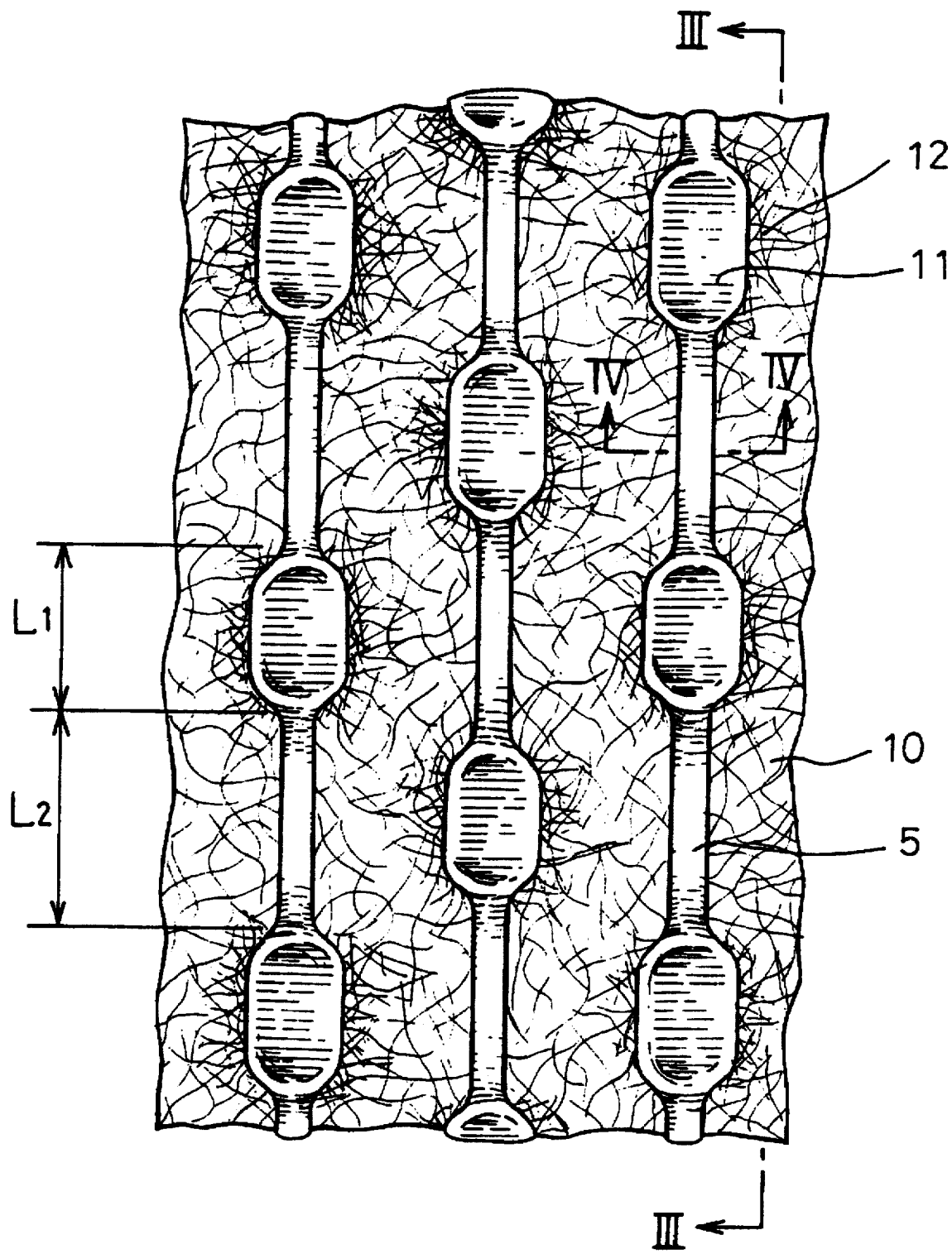
FIG. 2 is a fragmentary plan view showing, in an enlarged scale, the napkin.
Figure 3:
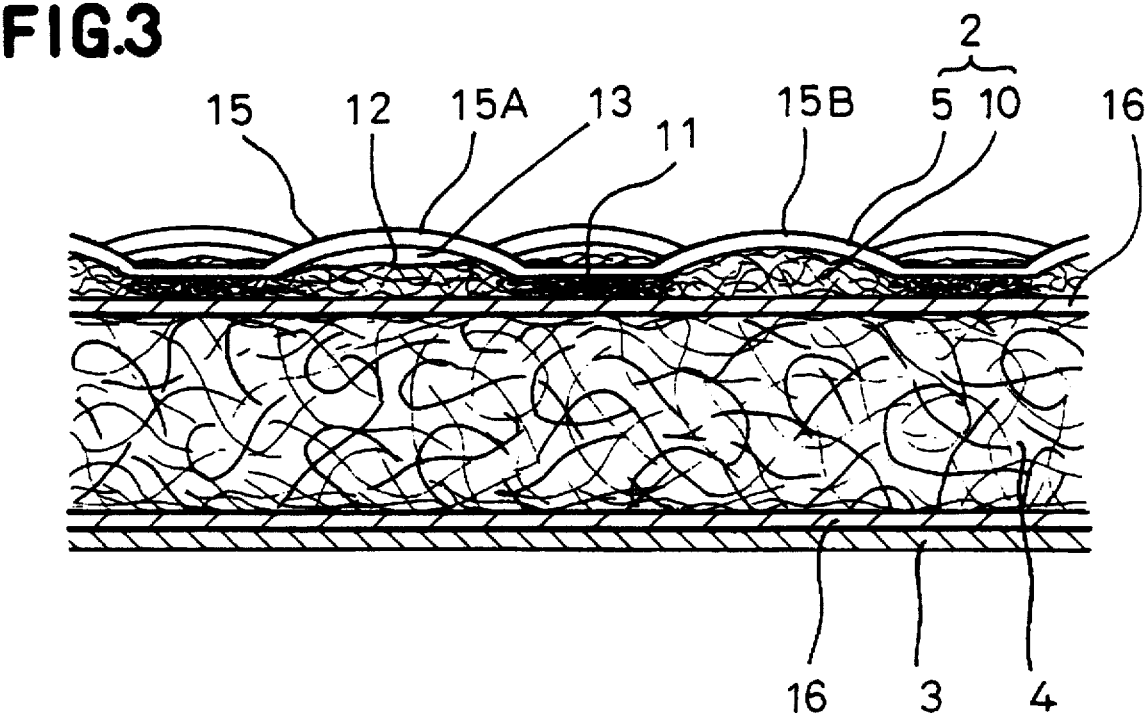
FIG. 3 is a sectional view taken along a line III—III in FIG. 2.

Referring to FIGS. 2 and 3, the topsheet 2 comprises a lower layer defined by a nonwoven fabric 10 and an upper layer defined by the filaments 5 which are welded to an upper surface 12 of the nonwoven fabric 10 at bonding zones 11 intermittently arranged longitudinally of the respective filaments 5 so that each filament 5 may form between each pair of adjacent the bonding zones 11 a bulge 15 describing a circular arc above the upper surface 12 of the nonwoven fabric 10. At the respective bonding zones 11, each filament 5 is relatively thin and flat and the nonwoven fabric 10 is compressed, i.e., the portions of the nonwoven fabric 10 underlying these bonding zones 11 are thinner than the portions surrounding them and have a correspondingly higher density. The bulges 15 are substantially circular in their radial cross-sections (See FIG. 4) and spaces 13 are formed or not between these bulges 15 and the upper surface 12 of the nonwoven fabric 10 (See the bulges 15A and 15B). The substantially circular cross-section should be understood to be the cross-sectional shape defined by a true circle, an ellipse or the other cross-sectional shape defined by any smooth curves. In such an arrangement of the topsheet 2, each filament 5 preferably has a diameter of 0.05 to 5 mm along the circular arcs of each bulge 15 and may cover preferably 5 to 95%, more preferably, 20 to 80% of the upper surface 12 of the nonwoven fabric 10 as viewed in the state of FIG. 2. The filaments 5 may be obtained by extrusion-molding synthetic resin such as polyethylene, polypropyrene, polyester, nylon, ethylene-vinylacetate copolymer or elastomer mixed, if desired, with filler such as titanium oxide, silica, calcium carbonate or talc and water repelling agent such as fluorocarbon resin. The nonwoven fabric 10 preferably contains thermoplastic synthetic resin fibres of 20 to 100% by weight which has a fineness of 0.5 to 8 d and a weight per unit area of 5 to 80 g/m². The nonwoven fabric 10 may be either hydrophobic or hydrophilic and, if desired, the hydrophobic fibres may be used after treated to become hydrophilic or the hydrophobic fibres may be mixed with the hydrophilic fibres of up to 80% by weight.

For bonding the filaments 5 to the nonwoven fabric 10, a length $L_1$ of each bonding zone 11 and a length $L_2$ of each bulge 15 are preferably dimensioned to be 0.3 to 2 mm and 0.5 to 3 mm, respectively.

Figure 4:
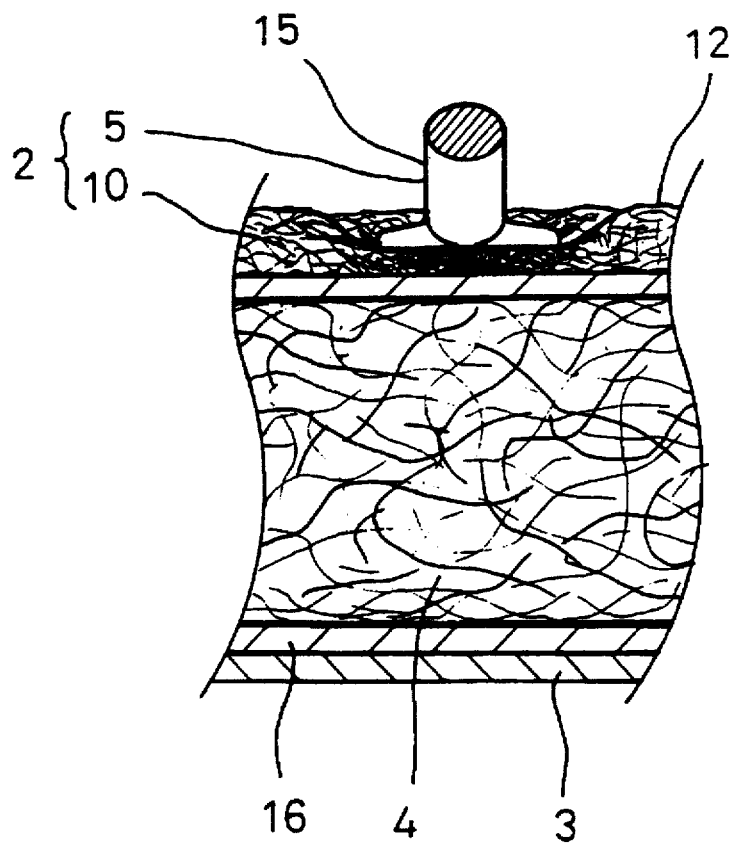
FIG. 4 is a sectional view taken along a line IV—IV in FIG. 2.

Referring to FIGS. 3 and 4, the backsheet 3 is made of a plastic film and the core 4 is made of fluff pulp or a mixture of fluff pulp and superabsorbent polymer particles, which has been appropriately shaped and covered with a tissue paper 16.

The sanitary napkin 1 having been illustrated and described may be used in the usual manner and most of menstrual discharge is absorbed by portions of the nonwoven fabric 10 defined between respective pairs of adjacent filaments 5. Menstrual discharge is guided also into the spaces 13 (See FIG. 3) directly underlying the bulge 15A of the filaments 5 and then absorbed through the nonwoven fabric 10 by the core 4. Compared to the conventional sanitary napkin in which the menstrual discharge having been absorbed by the core is distinctly visible through the topsheet, this novel napkin 1 is advantageous in that the filaments 5 partially covering the nonwoven fabric 10 contribute to alleviate undesirable visibility of the menstrual discharge having been absorbed by the core 4 through the topsheet when the used napkin 1 is thrown away.

Figure 5:
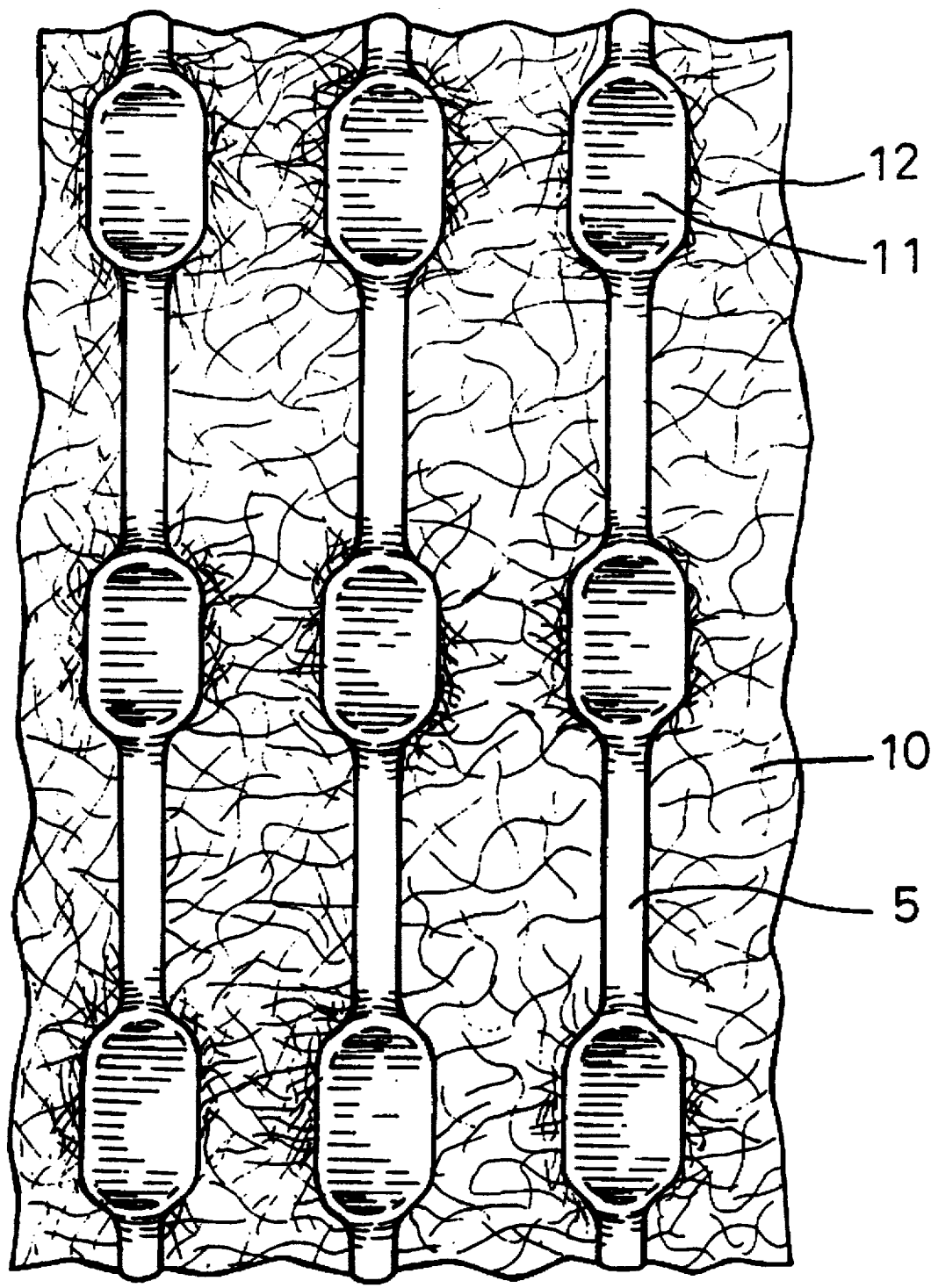
FIG. 5 is a view similar to FIG. 2 showing an embodiment of the composite nonwoven fabric.

Referring to FIG. 5, according to this topsheet, the bonding zones 11 of the respective filaments 5 are transversely aligned with one another. In the case of the filaments 5 arranged in a high density, i.e., at close intervals, the embodiment of FIG. 5 is advantageous in that the bonding zones 11 are reliably spaced from the adjacent bulges 15 and free from any interference with the expected function of the bulges 15. The topsheet 2 shown by FIGS. 2 and 5 may be produced by feeding a plurality of filaments 5 from an extruder onto the upper surface of the continuously fed nonwoven fabric and then embossing or, if necessary, heat-embossing these two components together.

The composite nonwoven fabric, according to the present invention, allows the body fluids absorptive articles such as the sanitary napkin employing this as the liquid-permeable topsheet to have a good cushioning effect, since the filament bulges describing the circular arcs are elastically deformed as they come in contact with the wearer's skin. Practically, only the tops of these filament bulges come in contact with the wearer's skin and these bulges are substantially circular in their radial cross-sections, so that a total area of the topsheet destined to come in contact with the wearer's skin is relatively small and, therefore, there is no apprehension that the wearer might suffer from an undesirable sticky feeling peculiar to plastics.

What is claimed is:

1. A liquid-permeable composite nonwoven fabric for use in body fluids absorptive articles comprising a liquid-permeable nonwoven fabric including thermoplastic synthetic fibers and a plurality of continuous filaments made of thermoplastic synthetic resin, said filaments bonded to an upper surface of said liquid-permeable fibrous nonwoven fabric, wherein:

said filaments extend longitudinally along said fibrous nonwoven fabric, said filaments being generally parallel to one another, each of said filaments fixedly attached to the upper surface of said fibrous nonwoven fabric at bonding zones, said bonding zones intermittently arranged along the longitudinally extending filaments so as to form, between each pair of adjacent said bonding zones along each of said filaments, a bulge forming a generally circular arc above the upper surface of said fibrous nonwoven fabric and having a substantially circular shape in its radial cross-section; and said bonding zones being relatively thin and flat, first portions of said nonwoven fabric underlying said bonding zones being thinner than second portions of said nonwoven fabric surrounding said first portions and having a higher density than that of the second portions.

2. A composite nonwoven fabric according to claim 1, wherein said filaments are welded to the upper surface of said nonwoven fabric.

3. A composite nonwoven fabric according to claim 1, wherein both said filaments and said nonwoven fabric are hydrophobic.

4. A composite nonwoven fabric according to claim 1, wherein said filaments are hydrophobic and said nonwoven fabric is hydrophilic.

5. The liquid permeable composite nonwoven fabric of claim 1, wherein said bonding zones of adjacent respective filaments are transversely aligned with one another.

6. A body fluids absorptive article, comprising a. a topsheet in the form of a liquid permeable composite non-woven fabric including thermoplastic synthetic fibers and a plurality of continuous filaments made of thermoplastic synthetic resin, said filaments bonded to an upper surface of said liquidpermeable fibrous nonwoven fabric, wherein:

said filaments extend longitudinally along said fibrous nonwoven fabric, said filaments being generally parallel to one another, each of said filaments fixedly attached to the upper surface of said fibrous nonwoven fabric at bonding zones, said bonding zones intermittently arranged along the longitudinally extending filaments so as to form, between each pair of adjacent said bonding zones along each of said filaments, a bulge forming a generally circular arc above the upper surface of said fibrous nonwoven fabric and having a substantially circular shape in its radial cross-section; and said bonding zones being relatively thin and flat, first portions of said nonwoven fabric underlying said bonding zones being thinner than second portions of said nonwoven fabric surrounding said first portions and having a higher density than that of the second portions;

b. a liquid impermeable backsheet; and c. a liquid absorbent core disposed between said topsheet and said backsheet;

wherein said topsheet and said backsheet are joined together along peripheral portions thereof extending outward beyond a peripheral edge of said core.

* * * * *